US009067982B2

(12) United States Patent
Vedamoorthy (10) Patent No.: US 9,067,982 B2
(45) Date of Patent: Jun. 30, 2015

(54) COMPOSITIONS AND METHODS FOR REDOX MODULATED PROTEINS (76) Inventor: Srikanth Vedamoorthy, New Albany, OH (US)

( * ) Notice: Subject to any disclaimer, the term of this patent is extended or adjusted under 35 U.S.C. 154(b) by 0 days.

(21) Appl. No.: 13/051,425

(22) Filed: Mar. 18, 2011

(65) Prior Publication Data
US 2011/0230649 A1    Sep. 22, 2011

Related U.S. Application Data (60) Provisional application No. 61/340,458, filed on Mar. 18, 2010.

(51) Int. Cl.
*C12N 9/00* (2006.01)
*C12N 9/99* (2006.01)
*C12N 9/96* (2006.01)
*C12P 21/06* (2006.01)
*C12P 21/04* (2006.01)
*C07K 16/18* (2006.01)
*C12P 21/02* (2006.01)

(52) U.S. Cl.
CPC . *C07K 16/18* (2013.01); *C12N 9/93* (2013.01); *C12P 21/02* (2013.01); *C12N 9/99* (2013.01); *C07K 2319/00* (2013.01); *C12N 9/96* (2013.01)

(58) Field of Classification Search
None
See application file for complete search history.

(56) References Cited

U.S. PATENT DOCUMENTS

2004/0105853 A1*   6/2004   Xiao ................... 424/94.64

* cited by examiner

*Primary Examiner* — Gary Nickol
*Assistant Examiner* — Lakia Tongue
(74) *Attorney, Agent, or Firm* — Standley Law Group LLP (57) ABSTRACT Disclosed embodiments relate to antibodies that recognize redox modulated proteins such as glutathionylated actin. Embodiments relate to a reagent for the immunoassay of glutathionylated actin. Disclosed embodiments also relate to diagnosis of and therapies for the treatment of diseases related to impaired deglutathionylation of peptides. Additionally, disclosed embodiments relate to pharmaceutical compositions containing antibodies which recognize redox modulated proteins and kits for the detection or treatment of diseases related to redox modulated proteins which include antibodies that recognize redox modulated proteins.

6 Claims, 7 Drawing Sheets

Residues 349 to 375 of SEQ ID NO:2

```
349     LSTFQQMWISK QEYDEAGPSIVHRKCF     375 Human
349     LSTFQQMWISK QEYDEAGPSIVHRKCF     375 Rat
349     LSTFQQMWISK QEYDEAGPSIVHRKCF     375 Mouse
                              *
```

|  | Rabbit # 2047 | | | Rabbit # 2048 | | | Rabbit # 2049 | | |
|---|---|---|---|---|---|---|---|---|---|
|  |  | Result after bleed | | | Result after bleed | | | Result after bleed | |
| Dilution | Pre-immun | 1st | 2nd | Pre-immun | 1st | 2nd | Pre-immun | 1st | 2nd |
| 1:1,000 | 0.073 | 2.789 | 2.840 | 0.055 | 2.905 | 2.414 | 0.108 | 2.767 | 2.576 |
| 1:2,000 | 0.059 | 2.747 | 2.785 | 0.054 | 2.895 | 2.091 | 0.064 | 2.758 | 2.445 |
| 1:4,000 | 0.042 | 2.658 | 2.690 | 0.037 | 2.885 | 1.691 | 0.059 | 2.699 | 2.174 |
| 1:8,000 | 0.051 | 2.482 | 2.534 | 0.051 | 2.795 | 1.233 | 0.067 | 2.553 | 1.996 |
| 1:16,000 | 0.050 | 2.114 | 2.434 | 0.051 | 2.608 | 0.785 | 0.053 | 2.383 | 1.520 |
| 1:32,000 | 0.052 | 1.416 | 2.204 | 0.060 | 2.55 | 0.462 | 0.054 | 1.884 | 1.082 |
| 1:64,000 | 0.054 | 0.871 | 1.736 | 0.056 | 2.118 | 0.273 | 0.070 | 1.289 | 0.676 |
| 1:128,000 | 0.062 | 0.483 | 1.034 | 0.061 | 1.474 | 0.176 | 0.080 | 0.707 | 0.376 |
| 1:256,000 | 0.045 | 0.272 | 0.635 | 0.048 | 0.886 | 0.120 | 0.057 | 0.392 | 0.247 |
| 1:512,000 | 0.057 | 0.169 | 0.348 | 0.066 | 0.563 | 0.099 | 0.075 | 0.273 | 0.159 |
|  |  |  |  |  |  |  |  |  |  |
| Titer | < 1:1,000 | 1:512,000 | 1:512,000 | < 1:1,000 | 1:512,000 | 1:64,000 | < 1:1,000 | 1:512,000 | 1:512,000 |

Figure 4

| Dilution | Rabbit #2048 | | Rabbit # 2049 | |
| --- | --- | --- | --- | --- |
| | Pre-immune | Final | Pre-immune | Final |
| 1:1,000 | 0.0065 | 1.01860 | 0.118 | 3.98920 |
| 1:2,000 | 0.0045 | 0.87710 | 0.094 | 3.93310 |
| 1:4,000 | 0.0039 | 0.70750 | 0.095 | 4.17390 |
| 1:8,000 | 0.0045 | 0.50508 | 0.087 | 3.87670 |
| 1:16,000 | 0.0071 | 0.28345 | 0.105 | 2.49310 |
| 1:32,000 | 0.0059 | 0.29705 | 0.094 | 1.43300 |
| 1:64,000 | 0.0065 | 0.19835 | 0.072 | 0.95632 |
| 1:128,000 | 0.0046 | 0.07265 | 0.083 | 0.51525 |
| 1:256,000 | 0.0034 | 0.03602 | 0.067 | 0.26192 |
| 1:512,000 | 0.0059 | 0.04538 | 0.075 | 0.18842 |

1. 0.5 µg protein
2. 1.0 µg protein
3. 2.5 µg protein
4. 2.5 µg protein reduced with β-ME

SEQUENCE LISTING

```
<160> NUMBER OF SEQ ID NOS: 2

<210> SEQ ID NO 1
<211> LENGTH: 377
<212> TYPE: PRT
<213> ORGANISM: Homo sapiens

<400> SEQUENCE: 1

Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125
```

```
Phe Asn Val Pro Ala Met Tyr Val Ala Ile Gln Ala Val Leu Ser Leu
            130                 135                 140
Tyr Ala Ser Gly Arg Thr Thr Gly Ile Val Leu Asp Ser Gly Asp Gly
145                 150                 155                 160
Val Thr His Asn Val Pro Ile Tyr Glu Gly Tyr Ala Leu Pro His Ala
                165                 170                 175
Ile Met Arg Leu Asp Leu Ala Gly Arg Asp Leu Thr Asp Tyr Leu Met
                180                 185                 190
Lys Ile Leu Thr Glu Arg Gly Tyr Ser Phe Val Thr Thr Ala Glu Arg
            195                 200                 205
Glu Ile Val Arg Asp Ile Lys Glu Lys Leu Cys Tyr Val Ala Leu Asp
            210                 215                 220
Phe Glu Asn Glu Met Ala Thr Ala Ala Ser Ser Ser Ser Leu Glu Lys
225                 230                 235                 240
Ser Tyr Glu Leu Pro Asp Gly Gln Val Ile Thr Ile Gly Asn Glu Arg
                245                 250                 255
Phe Arg Cys Pro Glu Thr Leu Phe Gln Pro Ser Phe Ile Gly Met Glu
                260                 265                 270
Ser Ala Gly Ile His Glu Thr Thr Tyr Asn Ser Ile Met Lys Cys Asp
            275                 280                 285
Ile Asp Ile Arg Lys Asp Leu Tyr Ala Asn Asn Val Leu Ser Gly Gly
            290                 295                 300
Thr Thr Met Tyr Pro Gly Ile Ala Asp Arg Met Gln Lys Glu Ile Thr
305                 310                 315                 320
Ala Leu Ala Pro Ser Thr Met Lys Ile Lys Ile Ala Pro Pro Glu
                325                 330                 335
Arg Lys Tyr Ser Val Trp Ile Gly Gly Ser Ile Leu Ala Ser Leu Ser
                340                 345                 350
Thr Phe Gln Gln Met Trp Ile Ser Lys Gln Glu Tyr Asp Glu Ala Gly
            355                 360                 365
Pro Ser Ile Val His Arg Lys Cys Phe
                370                 375

<210> SEQ ID NO 2
<211> LENGTH: 375
<212> TYPE: PRT
<213> ORGANISM: Homo sapiens

<400> SEQUENCE: 2

Glu Glu Glu Asp Ser Thr Ala Leu Val Cys Asp Asn Gly Ser Gly Leu
1               5                   10                  15
Cys Lys Ala Gly Phe Ala Gly Asp Asp Ala Pro Arg Ala Val Phe Pro
            20                  25                  30
Ser Ile Val Gly Arg Pro Arg His Gln Gly Val Met Val Gly Met Gly
                35                  40                  45
Gln Lys Asp Ser Tyr Val Gly Asp Glu Ala Gln Ser Lys Arg Gly Ile
            50                  55                  60
Leu Thr Leu Lys Tyr Pro Ile Glu His Gly Ile Ile Thr Asn Trp Asp
65              70                  75                  80
Asp Met Glu Lys Ile Trp His His Ser Phe Tyr Asn Glu Leu Arg Val
                85                  90                  95
Ala Pro Glu Glu His Pro Thr Leu Leu Thr Glu Ala Pro Leu Asn Pro
            100                 105                 110
Lys Ala Asn Arg Glu Lys Met Thr Gln Ile Met Phe Glu Thr Phe Asn
```

-continued

```
             115                 120                 125
Val Pro Ala Met Tyr Val Ala Ile Gln Ala Val Leu Ser Leu Tyr Ala
        130                 135                 140

Ser Gly Arg Thr Thr Gly Ile Val Leu Asp Ser Gly Asp Gly Val Thr
145                 150                 155                 160

His Asn Val Pro Ile Tyr Glu Gly Tyr Ala Leu Pro His Ala Ile Met
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Val Thr Thr Ala Glu Arg Glu Ile
        195                 200                 205

Val Arg Asp Ile Lys Glu Lys Leu Cys Tyr Val Ala Leu Asp Phe Glu
        210                 215                 220

Asn Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Thr Leu Phe Gln Pro Ser Phe Ile Gly Met Glu Ser Ala
            260                 265                 270

Gly Ile His Glu Thr Thr Tyr Asn Ser Ile Met Lys Cys Asp Ile Asp
            275                 280                 285

Ile Arg Lys Asp Leu Tyr Ala Asn Asn Val Leu Ser Gly Gly Thr Thr
        290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ala Gly Pro Ser
            355                 360                 365

Ile Val His Arg Lys Cys Phe
370                 375
```

COMPOSITIONS AND METHODS FOR REDOX MODULATED PROTEINS

CROSS-REFERENCE TO RELATED APPLICATIONS

This non-provisional patent application claims the benefit under 35 USC 119(e) of U.S. Provisional Application No. 61/340,458 filed Mar. 18, 2010, which is hereby incorporated by reference as if recited fully herein.

REFERENCE TO A SEQUENCE LISTING

A sequence listing in computer readable form (CRF) is on file. The sequence listing is in an ASCII text (.txt) file titled SEQ ID NO 2 ST25 created on Feb. 2, 2013 and 4 KB in size and is hereby incorporated by reference in its entirety.

TECHNICAL FIELD

Embodiments relate to systems, methods, and compositions for detecting redox modulated proteins. More specifically, embodiments relate to detecting glutathionylated proteins.

BACKGROUND

Detecting redox modulated proteins with specificity is critical to understand the mechanisms of redox homeostasis that are occurring in disease processes. Redox is a change in oxidation, and its occurrence signals a change in cell function. Only recently has research highlighted the importance of measuring the levels of these redox modulated proteins. Understanding these changes and detecting specifically where in disease processes they are occurring will be a key for the early intervention and prevention of further damage.

Because the significance of these proteins is a relatively new discovery, little advancement has been made in their detection. Currently available tools like analytical, proteomic approaches are not sensitive or cost effective or not compatible for direct visualization.

SUMMARY

Embodiments relate to unique antibodies that detect redox modulated proteins, and the development of related products. More specifically, disclosed embodiments relate to antibodies that specifically bind to glutathionylated proteins or fragments thereof. Antibodies which can detect redox modulated proteins provide novel opportunities for human disease research to help understand disease state and mechanism. The ability to detect these proteins will be a factor in research areas like cardiovascular diseases, inflammatory diseases, aging-related diseases like Parkinson's and Alzheimer's diseases, atherosclerosis, hypertension, carcinomas, and diabetes. Embodiments will open doors to unraveling the functional significance of protein modifications in human diseases where changes in redox balances have been documented.

Recent research has shown that increased levels of redox modulated proteins such as Protein S-Glutathionylation and Protein S-Nitrosylation are critical indicators of stress and disease states. The detection of these proteins facilitates understanding of the redox modification of a specific protein that undergoes redox modifications occurring early in disease processes, allowing earlier intervention in the disease process and the prevention of further damage. However, researchers currently lack methods and compositions for detecting and measuring the redox modulated proteins with specificity. Currently available tools such as analytical, proteomic approaches are not sensitive or cost effective. Better tools would be of tremendous benefit to researchers in a wide array of disease areas, including but not limited to cardiovascular diseases, inflammatory diseases, Parkinson's and Alzheimer's disease, atherosclerosis, hypertension, cancer, and diabetes.

Conjugation of glutathione to protein cysteinyl residues, called protein S-glutathionylation, is a critical mechanism in regulating the functions of enzymes, signaling molecules, transcription factors, heat shock proteins, ion channels, mitochondrial proteins, and cytoskeletal proteins. During oxidative stress GSSP level increases and are controlled by glutaredoxins under physiological conditions. This modification helps in protecting the protein from 1) irreversible oxidation and 2) modulation of protein function thus preserving the vital functions of the cells.

Impaired deglutathionylation of the functionally critical cysteine residues leads to protein inactiveness and thus impaired protein function. Due to the imbalance in glutathionlyation or deglutathionylation process the formation of GSSP is increased irreversibly in stress/disease conditions, which leads to protein adduct formation. S-glutathionylated proteins have been identified in the following human diseases; Actin—Ischemia/Cardiovascular disease and Friedreich's ataxia, Tau—Alzheimer's disease, Hemoglobin—Type 2 diabetes, CTFR—Cystic fibrosis, γ-S-crystallin—Cataract disease, Spectrin—Sickle cell anemia.

The present invention relates to methods and compositions for preventing, treating or ameliorating or detecting disease and/or symptoms related to redox modulated proteins including glutathionylated proteins to study the mechanisms involved in animal/human diseases comprising administering to an animal, preferably a human, an effective amount of one or more antibodies or fragments or variants thereof, or related molecules, that specifically bind to a redox modulated protein or a fragment or variant thereof. In specific embodiments, the present invention relates to methods and compositions for preventing, treating or ameliorating a disease or disorder associated with redox modulated proteins including glutathionylated proteins, comprising administering to an animal, preferably a human, an effective amount of one or more antibodies or fragments or variants thereof, or related molecules, that specifically bind a redox modulated protein or a fragment or variant thereof.

Another embodiment includes the use of antibodies disclosed herein as a diagnostic tool to monitor the presence of redox modulated proteins including glutathionylated proteins, for example GSS-actin.

The present invention also provides anti-GSSP antibodies that are coupled to a detectable label, such as an enzyme, a fluorescent label, a luminescent label, or a bioluminescent label. The present invention also provides a tool for the detection of redox modulated protein that could serve in finding a therapeutic agent. The present invention also provides redox modulated protein antibodies that are coupled, directly or indirectly, to a fluorescent tag/radioactive material. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

Embodiments relate to an isolated antibody recognizing a redox modulated protein, including recognizing a glutathionylated protein. Additionally, embodiments relate to antibodies recognizing glutathionylated actin.

Embodiments include a method for the glutathionylation of a peptide comprising mixing a peptide and an excess of glutathione in an appropriate solvent; and adding aldrithiol to the mixture.

Embodiments include a reagent for the immunoassay of glutathionylated actin comprising an isolated antibody.

DETAILED DESCRIPTION

Embodiments relate to systems, methods, and compositions for detecting redox modulated proteins. Various embodiments include methods and compositions for identifying S-glutathionylated proteins and exploring the cellular significance of these modifications with respect to those proteins, diagnosing diseases related to redox modulated proteins and methods and compositions for treating those diseases.

Cluster analysis of proteins susceptible to S-glutathionlyation is summarized below;

| Function | Protein |
|---|---|
| Energy metabolism | ATPase, NADPH, GAPDH, Pyruvate kinase, Pyruvate dehydrogenase, Phosphoglycerate kinase, Triose phosphate isomerase, aldolase, α-ketoglutarate dehydrogenase, Mitochondrial isocitrate dehydrogenase, Complex 1, NADH ubiquinone reductase, Carbonic anhydrase III, Catechol-O-methyltransferase |
| Cytoskeleton | Actin, Spectrin, Tubulin, Vimentin |
| Signaling | Creatinine kinase, PKC, PKG, cAMP dependent PKA, MEKK1 (JNK), Protein tyrosine phosphatase1B, PTEN, Pyrophosphatase 2A, NFκB, subunits 65 and 50, c-able, p53, Caspase 3, GTPase, p21 ras, Keap1, Nrf2 |
| Calcium homeostasis | SERCA, RyR I & II, S100A1, S100B, CTFR |
| Protein folding | HSP 65, 70, PDI, Ubiquitin conjugating enzyme, 20S Proteosome |
| Redox | Glutathione S-transferase, Nitric Oxide Synthases, Thioredoxin 1, Peroxiredoxin |

List of S-nitrosylated proteins in disease conditions is given below.

| Protein | Diseases |
|---|---|
| Dyanin related protein - 1, Parkin, Peroxiredoxin 2, Protein disulfide isomerase, X-linked inhibitor of apoptosis, Glyceraldehyde 3-phosphate dehydrogenase | Alzheimer's disease/Parkinson's disease |
| HIF-1 alpha | Angiogenesis/pulmonary arterial hypertension |
| Ras | Adaptive immunity/tumor maintenance |
| Arginase, glutathione | Asthma/Endothelial dysfunction |
| Glutathione | Cystic Fibrosis |
| Cardiac Ryanodine receptor, Nitric Oxide Synthases | Heart failure |
| Insulin receptor beta, Insulin receptor substrate 1, Protein kinase b | Diabetes (Type II) |
| Hemoglobin | Type I Diabetes/Pulmonary arterial hypertension/Sickle cell anemia |
| Serum Albumin | Preeclampsia |
| Ryanodine receptor 1 | Muscle fatigue/muscular dystrophy (duschenne)/Sudden cardiac death |
| Matrix metalloproteinase 9 | Stroke |

A list of antibody sets for heart and cardiovascular related research follows:

I. Hypertrophy Markers:
1) ANF—Artrial natriuretic factor/peptide
2) BNF—brain natriuretic factor/peptide
3) alpha-MHC/myosin-heavy chain
4) B-MHC
5) Phospholamban (PLN)
6) SERCA2A
7) PGC1-alpha II. Cardiac Defense:
1) Sod-1
2) Catalase
3) Gpx-1
4) G6PDH
5) GSR
6) Thoredoxin-1
7) Gamma-GCS III. Cardiac Stress/Chaperones:
1) Hsp 22/alpha-B-Crystallin
2) Hsp 25/Hsp 27 (in rat and human)
3) Hsp 47 (cardiac remodeling)
4) Hsp 70 (constitutive)
5) Hsp 70i (inducible)
6) Hsp 90 (gene regulation)
7) Hsp20/cvHSP (cardiovascular HSP)

IV. Cardiac Hypertrophy/Signaling:
1) Akt/p-Akt
2) GSK3-alpha
3) GSK3-B
4) ERK 1/2
5) p-ERK 1/2
6) Map38/41 and phospho V. Cardiac Gene-Regulation:
1) Hsp90
2) Hdac-1
3) Hdac-3
4) Hdac-4
5) Hdac-5
6) Hdac-6

VI. Cardiac Oxidative Stress Markers:
1) DNPH (protein oxidation)
2) Nitrotyrosine
3) Glutathione (s-glutathionylation)
4) Ubiquitin (ubiquitination)
5) Proteasome-21 (proteasome dysfunction)

VII. Cardiac Mitochondrial Stress/Biogenesis:
1) PGC1-alpha
2) Hsp-60
3) Sod-2
4) Thioredoxin-2
5) Aconitase VIII. Cardiac Mito Dysfunction:
1) Complex-1—sub units (set of 6)
2) Complex-3—sub units—(set of 6)
3) VDAC (voltage dependent anion channel)—MPTP opening
4) ANT (adenine nucleotide translocase)—MPTP
5) Cyclophilin-D—MPTP IX. Hypertension/Cardiac Hypertrophy:
1) TNF-alpha
2) TNF-alpha Receptro 1
3) TNF-alpha receptor 2
4) Nox-2/Gp91 phox
5) Nox-4/Gp21 phox
6) IL-6
7) IL-10

X. Cardiac NO Related:
1) eNOS
2) p-eNOS
3) Endothelin-1
4) Endothelin-receptor—A/ET-ra
5) Endothelin-receptor—B/ET-rb XI. Cardiac Apoptosis:
1) Bcl-2
2) Bax
3) Caspase-3
4) Cleaved caspase-3
5) Caspase-9
6) AIF (apoptosis inducing factor)

Figure 1:
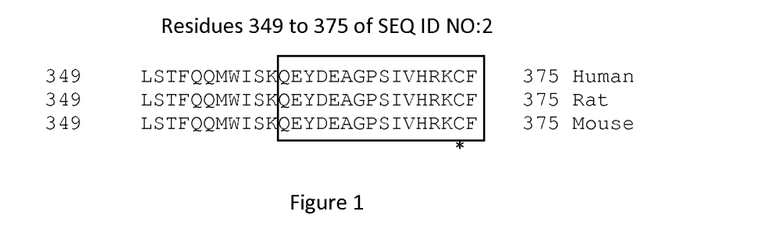
FIG. 1 is a side-by-side comparison of cardiac actin residues 349 to 375 of SEQ ID NO:2 across selected species.

FIG. 1 is a side-by-side comparison of cardiac actin, residues 349 to 375 of SEQ ID NO:2. The figure illustrates the high similarity in the amino acid sequence of the cardiac actin of different species, and the reactive cysteine target for glutathionylation.

The sequence for human actin which has been submitted in CRF under the file name SEQ ID NO 1_ST25 is hereby incorporated by reference in its entirety. The file was created on 15 Apr. 2011 and is 4 KB in length.

Unless otherwise defined, all technical and scientific terms used herein have the same meaning as commonly understood by one of ordinary skill in the art to which these embodiments pertain. Although methods and materials similar or equivalent to those described herein can be used in the practice or testing of various embodiments, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The section headings used herein are for organizational purposes only and are not to be construed as limiting the described subject matter in any way. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

As used herein, the term "subject" is intended to include humans, non-human animals, and plants. The term "non-human animals" includes all vertebrates, e.g., mammals and non-mammals, such as non-human primates, pigs, chickens and other birds, mice, dogs, cats, cows, and horses.

The antibody according to the present invention includes a polyclonal antibody, a monoclonal antibody, a chimeric antibody, a single chain antibody (scFv), a humanized antibody and a multispecific antibody. Also, the fragment of the antibody according to the present invention includes an antibody fragment such as Fab, Fab', $F(ab')_2$, Fc, and Fv.

By "isolated antibody" is intended an antibody removed from its native environment. Thus, an antibody produced by, purified from and/or contained within a hybridoma and/or a recombinant host cell is considered isolated for purposes of the present invention.

For a polyclonal antibody, blood can be taken from a mammal sensitized with an antigen and blood serum can be isolated with known procedures from the blood to yield blood serum containing the polyclonal antibody. As needed, a fraction containing the polyclonal antibody can further be isolated from this blood serum.

For a monoclonal antibody, antibody-producing cells are taken from spleen or lymph-node of a mammal sensitized with the above-mentioned antigen, and then undergo cell fusion with myeloma cell. The resultant hybridoma is subjected to cloning and the antibody was recovered from the culture thereof to yield the monoclonal antibody.

A fragment of the abnormal protein can be used as an immunogen. Alternatively, the synthesized one based on the amino acid sequence of the abnormal protein can be used. The antigen can be used as a complex with a carrier protein. A variety of condensing agents can be used for preparation of the complex between the antigen and the carrier protein, which condensing agents include glutaraldehyde, carbodiimide, and maleimide active ester. The carrier protein may be a usually used one such as bovine serum albumin, thyroglobulin, and hemocyanin. A procedure for coupling at a rate (volume) of 1 time to 5 times is usually employed.

Examples of the animal immunized include mice, rats, rabbits, guinea pigs, hamsters. An example of a method of inoculation is subcutaneous, intramuscular or intraperitoneal administration.

The antibody-producing cells obtained from the spleen or lymph-node of the animal immunized undergo cell fusion with myeloma cells, and is isolated as hybridoma. As the myeloma cells, cells derived from mouse, rat, Homo sapiens and etc. are used. It is preferred that antibody-producing cell be derived from the same species. Yet there are cases where the cell fusion can be carried out between different species.

Procedures for the cell fusion may be carried out with a known method, in accordance with, for example, *Nature*, 256, 495, 1975. Examples of fusion accelerator include polyethylene glycols and Sendai virus. The cell fusion can be usually carried out by using about 20 to 50% of concentration of polyethylene glycols (average molecular weight 1000 to 4000); at a temperature of 20 to 40° C., preferably 30 to 37° C.; at a ratio in number of cells between antibody production cells and myeloma of usually about 1:1 to 10:1, and for about 1 to 10 minutes.

Various immunochemical methods can be employed for screening the antibody-producing hybridoma. Examples thereof include ELISA method using a microtiter plate coated with the abnormal protein, EIA method using a microtiter plate coated with an anti-immunoglobulin antibody, immune blot method using a nitrocellulose blotting membrane after electrophoresis of samples containing the abnormal protein.

Using such wells, cloning by, for example, a limiting dilution method can be further carried out to obtain a clone. Selection and breeding of the hybridoma is usually carried out culture medium for mammalian cells (such as RPMI1640) and supplemented with HAT (hypoxanthine, aminopterin, and thymidine). The clone obtained in such a way is intraperitoneally transplanted into a SCID mouse previously administrated with pristine. Ten to fourteen days later, ascites containing the monoclonal antibody at a high concentration is obtained, which ascites can be used as a raw material for antibody purification. Also the clone may be cultured and the obtained culture may be used as a raw material for antibody purification Any purification method may be used for purifying the monoclonal antibody as long as it is a known method for purifying an immunoglobulin. The purification can be readily accomplished by, for example, an ammonium sulfate fractionation method, a PEG fractionation method, an ethanol fractionation method, and use of an anion exchanger, as well as means such as affinity chromatography using the abnormal protein.

Purification of the polyclonal antibody from serum can be carried out in the same manner.

Also provided are various kits for performing the methods provided herein. Additionally, the kit may include instructional materials for performing various methods presented herein. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on an internet web site or may be distributed to the user as an electronic mail. When a kit is supplied, the different components can be packaged in separate containers. Such packaging of the components separately can permit long term storage without losing the active components' functions.

Unless otherwise defined in the specification, specific binding by an antibody to a redox modulated protein, such as glutathionylated actin, means that an antibody binds the redox modulated protein but does not significantly bind to (i.e., cross react with) proteins other than the redox modulated protein, such as other proteins in the same family of proteins). An antibody that binds the redox modulated protein and does not cross-react with other proteins is not necessarily an antibody that does not bind said other proteins in all conditions; rather, the redox modulated protein-specific antibody of the invention preferentially binds the redox modulated protein compared to its ability to bind other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Additionally, redox modulated protein-specific antibodies of the invention may bind modified forms of the redox modulated protein, for example, fusion proteins. In such a case when antibodies of the invention bind fusion proteins, the antibody must make binding contact with the redox modulated protein moiety of the fusion protein in order for the binding to be specific. Antibodies that specifically bind to the redox modulated protein can be identified, for example, by immunoassays or other techniques known to those of skill in the art.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab').sub.2 fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities. Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31 and Frigerio et al., (2000) Plant Physiology 123:1483-94, both of which are hereby incorporated by reference in their entireties.). ScFv dimers can also be formed through recombinant techniques known in the art; an example of the construction of scFv dimers is given in Goel et al., (2000) Cancer Research 60:6964-6971, which is hereby incorporated by reference in its entirety. Antibody multimers may be purified using any suitable method known in the art, including, but not limited to, size exclusion chromatography.

The term "variant" as used herein refers to a polypeptide that possesses a similar or identical amino acid sequence as a redox modulated protein polypeptide, a fragment of a redox modulated protein polypeptide, a redox modulated protein antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of redox modulated protein polypeptide such as GSS-actin, a fragment of a redox modulated protein polypeptide, a GSS-actin antibody or antibody fragment thereof.

The term "derivative" as used herein, refers to a variant polypeptide of the invention that comprises, or alternatively consists of, an amino acid sequence of a redox modulated protein polypeptide, a fragment of a redox modulated protein polypeptide, or an antibody of the invention that specifically binds to a redox modulated protein polypeptide, which has been altered by the introduction of amino acid residue substitutions, deletions or additions. The term "derivative" as used herein also refers to a redox modulated protein polypeptide, a fragment of a redox modulated protein polypeptide, an antibody that specifically binds to a redox modulated protein polypeptide which has been modified, e.g., by the covalent attachment of any type of molecule to the polypeptide. For example, but not by way of limitation, a redox modulated protein polypeptide, a fragment of a redox modulated protein polypeptide, or a redox modulated protein antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a redox modulated protein polypeptide, a fragment of a redox modulated protein polypeptide, or a redox modulated protein antibody, may be modified by chemical modifications using techniques known to those of skill in the art, including, but not limited to, specific chemical cleavage, acetylation, formylation, metabolic synthesis of tunicamycin, etc. Further, a derivative of a redox modulated protein polypeptide, a fragment of a redox modulated protein polypeptide, or a redox modulated protein antibody, may contain one or more non-classical amino acids. A polypeptide derivative possesses a similar or identical function as a redox modulated protein polypeptide, a fragment of a redox modulated protein polypeptide, or a redox modulated protein antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of a redox modulated protein, or a redox modulated protein antibody (including molecules such as scFv's, that comprise, or alternatively consist of, antibody fragments or variants thereof) that specifically binds to a redox modulated protein such as GSS-actin.

Antibodies of the present invention are preferably provided in an isolated form, and preferably are substantially purified. By "isolated" is intended an antibody removed from its native environment. Thus, for example, an antibody produced and/or contained, within a recombinant host cell is considered isolated for purposes of the present invention.

In certain embodiments, the antibodies of the present invention specifically bind a redox modulated protein polypeptide. An antibody that specifically binds redox modulated protein may, in some embodiments, bind fragments, variants (including species orthologs of redox modulated proteins), multimers or modified forms of redox modulated proteins. For example, an antibody specific for GSS-actin may bind the GSS-actin moiety of a fusion protein comprising all or a portion of the redox modulated protein.

Redox modulated proteins may be found as monomers or multimers (i.e., dimers, trimers, tetramers, and higher multimers). Accordingly, the present invention relates to antibodies that bind redox modulated proteins found as monomers or as part of multimers. In specific embodiments, antibodies of the invention bind redox modulated protein monomers, dimers, trimers or heptamers. In additional embodiments, antibodies of the invention bind at least dimers, at least trimers, or at least tetramers containing one or more redox modulated protein polypeptides.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. As such, disclosed embodiments relate to antibodies resulting from the introduction of peptides or polypeptides bearing an antigenic epitope used to mimic the native protein.

A variety of host-expression vector systems may be utilized to express the antibody molecules of this application. Such host-expression systems represent vehicles by which the coding sequences of interest may be produced and subsequently purified, but also represent cells which may, when transformed or transfected with the appropriate nucleotide coding sequences, express an antibody molecule of the invention in situ.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art. For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2560, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

In a preferred embodiment, antibodies of the invention preferentially bind GSS-actin, or fragments and variants thereof relative to their ability to bind other antigens. An antibody's ability to preferentially bind one antigen compared to another antigen may be determined using any method known in the art.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab).sub.2 fragment, or a portion thereof. Methods for fusing or conjugating polypeptides to antibody portions are known in the art.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates).

The present invention further encompasses antibodies (including antibody fragments or variants thereof), conjugated to a diagnostic or therapeutic agent. The antibodies can be used, for example, as part of a clinical testing procedure to, e.g., determine the safety or efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and known suitable radioactive materials.

Antibodies of the present invention may be used, for example, but not limited to, to purify, detect, and target redox modulated proteins, including both in vitro and in vivo diagnostic and therapeutic methods. For example, the antibodies have use in immunoassays for qualitatively and quantitatively measuring levels of redox modulated proteins in biological and non-biological samples.

One or more antibodies of the present invention (including molecules comprising, or alternatively consisting of, antibody fragments or variants thereof) that specifically bind to redox modulated proteins may be used locally or systemically in the body as a prophylactic or a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for treating individuals for diseases related to redox modulated proteins such as those diseases noted above.

Various delivery systems are known and can be used to administer antibody or fragment or variant thereof of the invention, e.g., encapsulation in liposomes, microparticles, microcapsules, recombinant cells capable of expressing the antibody or antibody fragment. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration, are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. The present invention provides kits that can be used in the above methods. In one embodiment, a kit comprises an antibody of the invention, preferably a purified antibody, in one or more containers.

EXAMPLES

The following examples are included to demonstrate embodiments. It should be appreciated by those skilled in the art that the techniques disclosed in the examples which follow represent techniques discovered by the inventors to function well in practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

General Methods

Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. The nomenclatures utilized in connection with, and the laboratory procedures and techniques of described herein are those well known and commonly used in the art. Antibodies: A Laboratory Manual, Ed Harlow, David Lane (1988); (Cold Spring Harbor Press, 1988).

Currently available tools like analytical, proteomic approaches are not either sensitive or cost effective. Hence, it is anticipated that the development of protein specific antibodies will provide novel opportunities for both basic and human disease research, which will help in understanding disease mechanism/state to the full extent. Identification of S-glutathionylated proteins and exploration of the cellular significance of this modification are really still in their infancy due to insufficient molecular tools like protein specific antibodies. The detection facilitates understanding the redox mechanism of a specific protein that undergoes redox modifications occurring early in disease processes, allowing earlier intervention and the prevention of further damage.

Antigen Preparation

Synthesis of Immunogen:

Cross-linking glutathionylated peptide with KLH was achieved by using SoluLink's HydraLink bioconjugation technology, which is based on two unique heterobifunctional linkers; 6-hydrazinonicotinamide (HyNic) and 4-formylbenzamide (4FB), attached to the peptide and KLH, respectively. SEQUENCE ID NO:2, having HyNic at its c-terminus was purchased from a commercial vendor and glutathionylated using aldrithiol as follows: 100 µM peptide and 1 mM GSH was mixed with 800 µM aldrithiol (Sigma-Aldrich, MO) in Tris buffer (100 mM pH 7.5). Aldrithiol was added dropwise. The reaction was done at RT with constant stirring. Linking KLH with 4FB was achieved by mixing the 1.5 µM KLH with 2.5 mM of 4FB, as per the guidelines of Solulink.

Figure 2A:
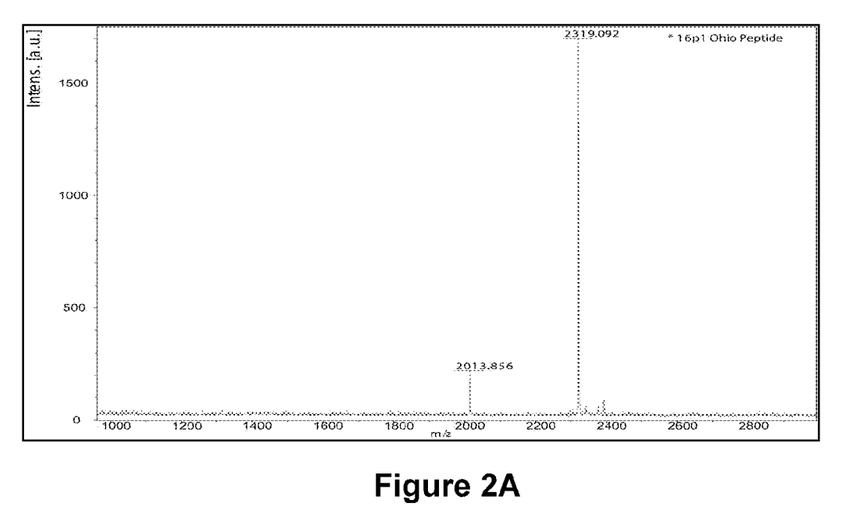
FIG. 2A is a mass spectrometric graph of glutathionlated and native protein.

FIG. 2A shows that mass spectrometric data indicates the effective glutathionylation of actin peptide. The observed mass of GSS-actin 374 peptide (2319) and unmodified actin peptide (2013) well correlated with expected mass.

Figure 2B:
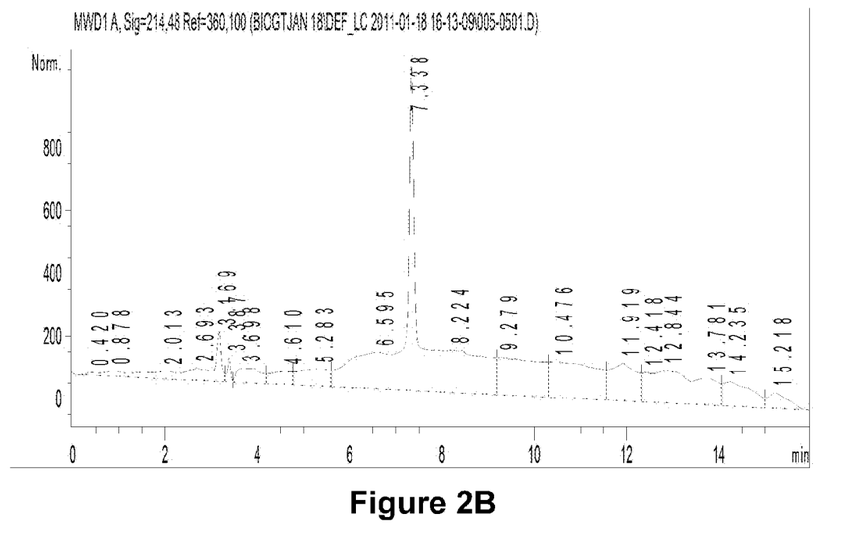
FIG. 2B is an analytical HPLC of purified glutathionylated protein.

FIG. 2B is an analytical HPLC profile of purified GSS-actin 374 peptide showing the efficient semi prep-HPLC purification. The peptide was cross linked with 4FB-KLH. HyNic-GSS-actin peptide and 4FB-KLH were reacted in phosphate buffer (2 mM, pH 6.0) for 24 hrs at 25° C. on rotary shaker. Concentration and purification of antigen was performed by using the Millipore's centrifugal filter units (MWCO 10,000). The KLH coupled peptide [(KLH-4FB)-(HyNic-GSHPeptide)] was used for immunization.

Figure 3:
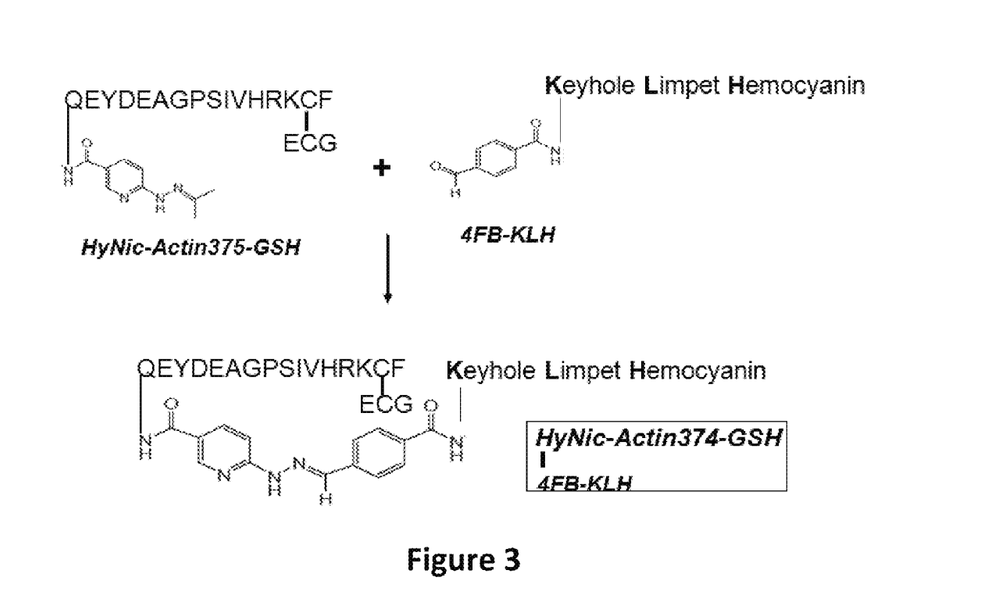
FIG. 3 is a chemical scheme showing actin antigen synthesis.

FIG. 3 depicts the antigen synthesis based on the specificity of chemical reaction between HyNic and 4-formylbenzamide (4FB), which forms the very stable bisaryl hydrazone conjugate. First, the 4FB, KLH conjugation was performed and linked with the HyNic GSS-actin peptide.

Rabbit serum collected at intervals after immunization was tested for reactivity to the actin/GSS-actin peptide (2 µg) coated on ELISA plate wells. A biotinylated peptide comprising biotin covalently attached to a peptide fragment comprising residues 360 to 375 of SEQ ID NO:2 was purchased from Ohio Peptides, was glutathionylated using aldrithiol, as mentioned earlier. Antibody titer was determined by standard ELISA protocol.

Enzyme-Linked Immunosorbent Assay (ELISA)

Nunc-Immuno MaxiSorb 96 well plates (Nunc, Denmark) were coated with 214/well actin or GSS-actin 374 in 10 mM PBS buffer, pH 7.4. After blocking with 0.1% BSA (Sigma-Aldrich, MO) in PBS-Tween 20 (0.05%) at 37° C. for 2 h, anti-GSSact 374 as antibody (affinity-purified to GSH-peptide) or pre-immune serum control (pre-I) were diluted 1/100 to 1/512,000 and added to the wells in 100 µl volume. Secondary antibody was peroxidase-conjugated goat anti-rabbit immunoglobulin (Millipore, Calif.) at 1/10000. TMB peroxidase substrate system solution (Millipore, Calif.) was added and color development was terminated after 4 minutes using 1M HCl. Absorbance at 450 nm was detected using a GENios pro plate reader (Tecan, N.C.).

Immunocytochemistry

Cells (Bovine Aortic Endothelial cells, BAECs) grown on sterile coverslips were treated/untreated with menadione (100 µM) for 1 hr, were fixed with 3.7% paraformaldehyde and permeabilized with 0.25% TritonX-100 in 1×TBS-Tween 20 (0.01%). Non-specific binding was blocked with 10% normal goat serum (Vector Labs, CA.) for 1 hr and exposed to actin/GSS-actin antibody for 3 hrs at 37° C. Secondary antibody (anti-rabbit IgG-Alexa Flour 488 and anti-mouse IgG-Alexa Flour 568) were used at 1:1000 dilution (Molecular probes, CA). Fluoromount-G (Southern Biotechnolgy) was used to attach coverslips to slides. The fluorescence was viewed using a confocal microscope equipped with epi-illuminescence using 60× objective.

Antibody Production and Purification

General Procedures for Immunizing Rabbits with GSS-Actin: Polyclonal Antibody Production Procedures used are based on standard express antibody protocols (GenScript, N.J.) for generating polyclonal antibodies.

The GSH-peptides were stored protected from light and oxygen until use.

Procedure

Basal (pre-immune) serum is collected on the day (1) before immunization.

Following collection of pre-immune serum, New Zealand White female rabbits were immunized by intradermal injection of 500 µg peptide plus T-Max adjuvant at multiple sites, intramuscular injection. After 2 weeks, an additional 250 µg of peptide was administered and after another 2 weeks another 250 µg of peptide was administered. The anti GSS-actin serum was affinity-purified by coupling 4 mg GSH-peptide-biotin to per milliliter Strepavidin UltraLink resin plus (Pierce, Rockford, Ill.) according to manufacturer's instructions.

day 1: 500 µg GSH-peptide per rabbit is freshly dissolved in phosphate buffered saline (PBS) and mixed with T-Max adjuvant (GenScript, N.J.) and used as antigen. Immunization is by intradermal injection at multiple sites (at least 10 sites) along the dorsum.

day 14: 250 μg peptide/rabbit is freshly dissolved in PBS and mixed with T-Max adjuvant (tot. vol. 1 ml or less). Injections are intradermal on the back (at least 10 sites).
day 21: bleed for serum. Test antibody titers by ELISA.
day 28: Immunization with 250 μg peptide/rabbit as day 21.
day 35: Test bleed for serum and ELISA.
day 38: Final bleed.

Figure 4:
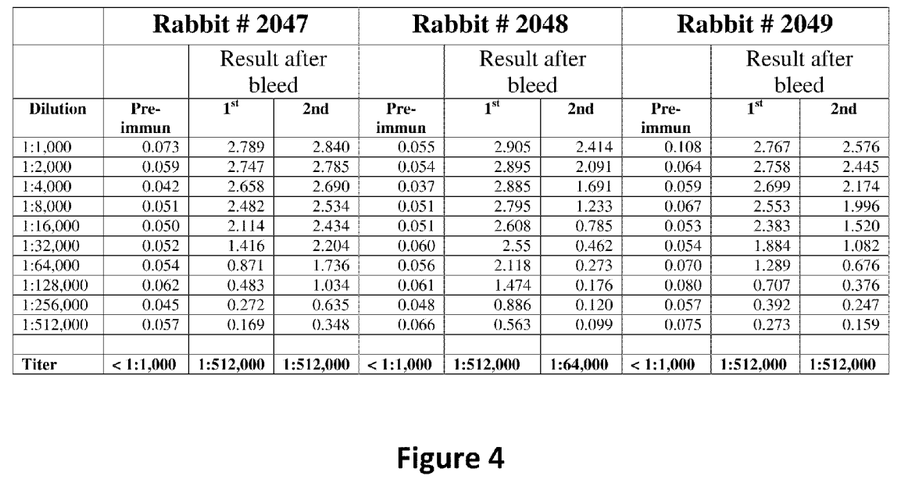
FIG. 4 is a table showing the results of an ELISA titer.

FIG. 4 is a table showing the results of an ELISA titer. ELISA titer result indicates that the rabbits immunized were very responsive and have generated high titer of antibodies (1:512,000) for non-glutathionylated actin (act374) peptide.

Figure 5:
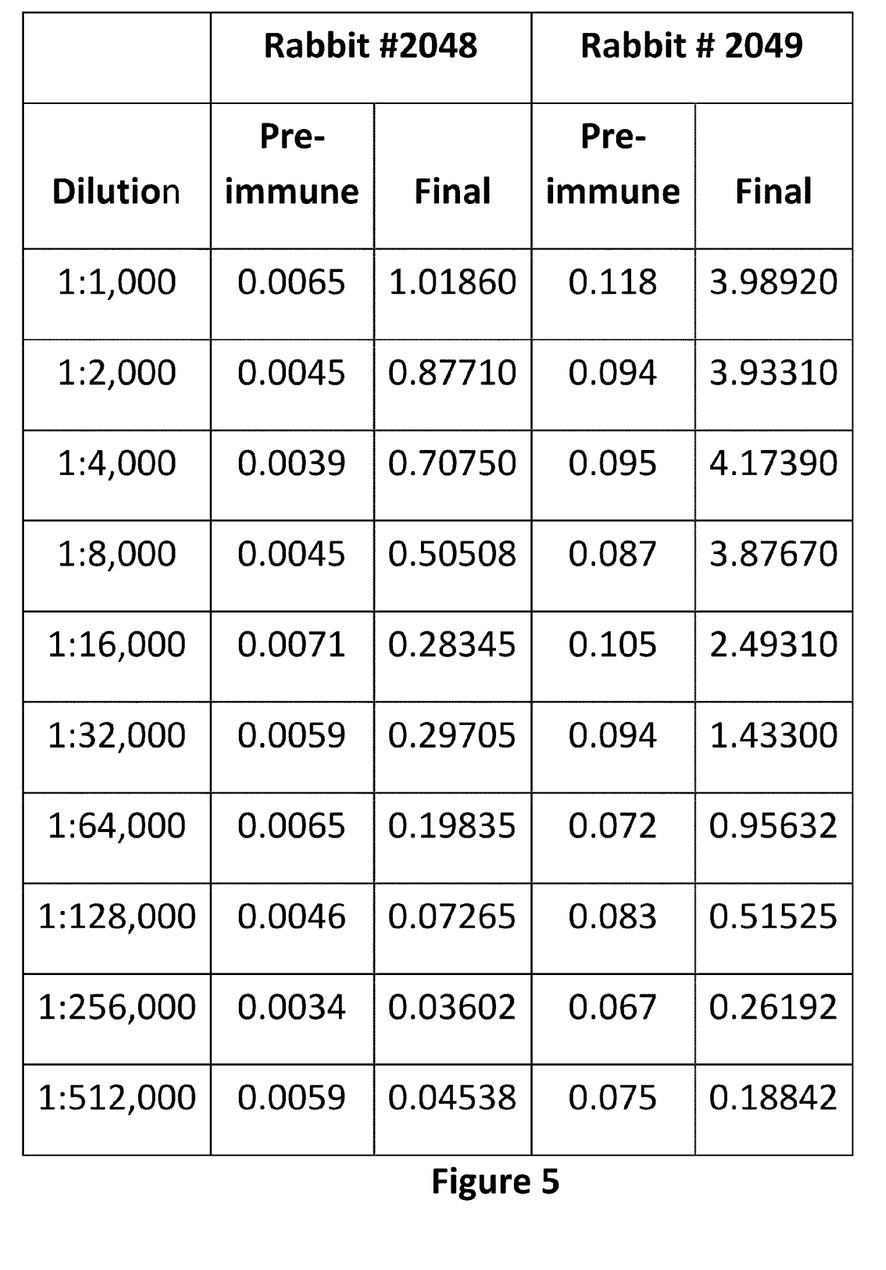
FIG. 5 is a table showing the results of the GSS-actin ELISA titer.

FIG. 5 is a table showing the results of the GSS-actin ELISA titer. ELISA titer result of GSS-actin (GSS-act374, 2 μg coated) showed relatively less antibody titer in rabbit #2048, compared to rabbit #2049. Thus, serum from rabbit #2049 was used for purification of antibody.

Antibody Purification

Immunoaffinity column was prepared by co-incubating 4 mg biotin-actin/GSS-actin with 1 ml of packed Strepavidin UltraLink plus resin (Pierce, Ill.) as per batch format protocol of Pierce. Briefly, 2 ml of 50% slurry resin was washed twice with thrice the volume of PBS, centrifuging at 5,000×g for 1 min. 4 mg biotin-actin/GSS-actin was mixed with 1 ml washed Strepavidin UltraLink plus resin, in a rotary rocker 1 hr at room temperature. Unbound biotin peptide was removed by washing with PBS-Tween (0.05%). 750 μl serum was incubated with the resin in a rotary shaker at 4° C. O/N. Resin/serum mix was poured in the column and unbound antibody is collected and labeled as flow-through. Column was washed with 10 ml of PBS-Tween (0.05%). The antibody bound in the column was purified using 5 ml of 0.1 M glycine. HCl (pH 2.8) and neutralized immediately using 1 M Tris, pH 8.0. Flow-through from the actin peptide column was co-incubated with the resin having GSS-actin peptide and the antibody specific to glutathionylated actin was eluted as GSS-actin antibody, mentioned earlier in this paragraph.

Figure 6:
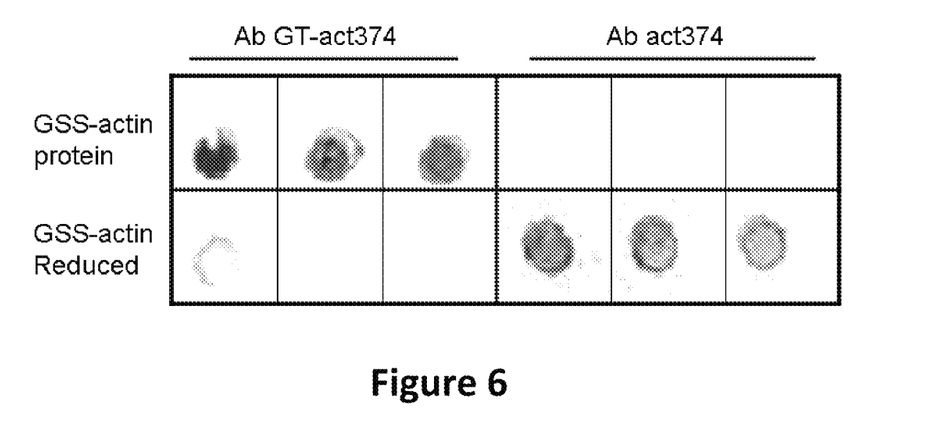
FIG. 6 is a Dot-blot analysis of glutathionylated and reduced glutathionylated actin.

FIG. 6 shows the results of a dot-blot assay. Dot-blot result indicates the antibody purified (Ab GT-act374) is specific and doesn't cross react with non-glutathionylated actin protein. Presence of signal only in the GSS-actin protein (not in actin protein) coated and reacted with Ab GT-act374 shows efficient purification from antibody for act374 (non-glutathionylated actin).

Figure 7:
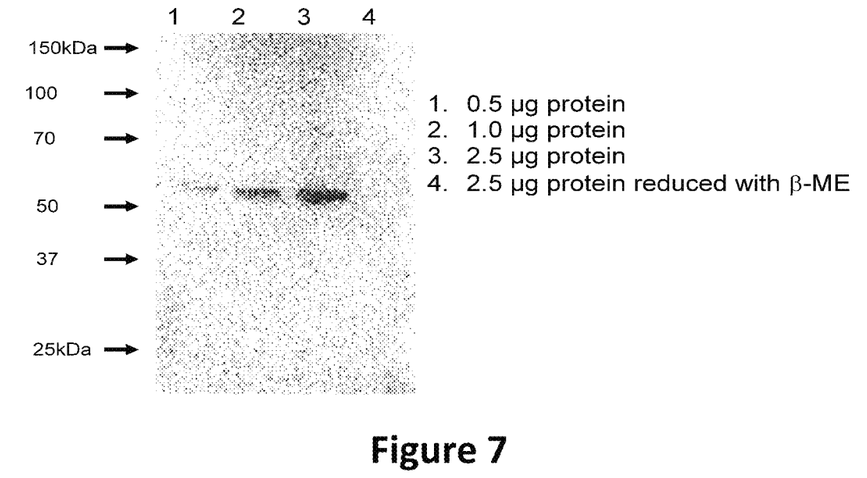
FIG. 7 shows the results of glutathionylated bovine cardiac actin probed with Ab GT-act374.

FIG. 7 shows the results of glutathionylated bovine cardiac actin probed with Ab GT-act374. The presence of quantity dependent signal in western blot analysis of purified bovine cardiac actin-glutathionylated (0.5, 1.0. 2.5 μg) and absence of signal in β-mercaptoethanol reduced GSS-actin (2.5 μg) probed by Ab GT-actin374, indicates quantitative and qualitative capability of detection methods using the disclosed antibody.

Figure 8:
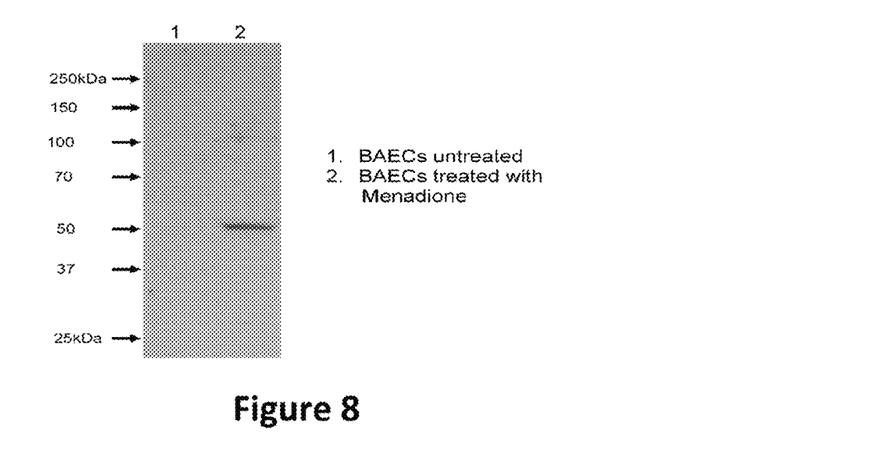
FIG. 8 shows the results of menadione treated bovine aortic endothelial cell protein probed with Ab GT-act374.

FIG. 8 shows the results of menadione treated bovine aortic endothelial cell protein probed with Ab GT-act374. The Figure shows the high specificity of Ab GT-act374, which recognized the GSS-actin formed in bovine aortic endothelial cells (BAECs) due to the treatment of 100 μM menadione for 1 hr.

Figure 9:
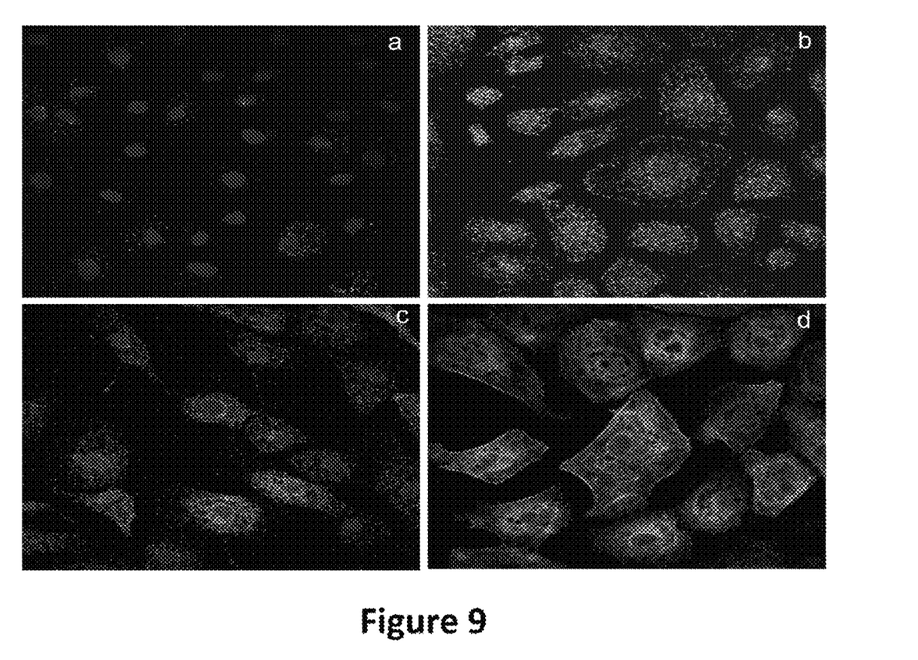
FIG. 9 shows the immunocytochemical localization of GSS-actin [(a) control, (b) treated] and actin [(c) control, (d) treated] using Ab GT-actin374 and Ab actin374.

FIG. 9 shows the immunocytochemical localization of GSS-actin [(a) control, (b) treated] and actin [(c) control, (d) treated] using Ab GT-actin374 and Ab actin374. Immunocytochemical staining studies using the Ab GT-act374 and Ab act374 shows clear difference in staining pattern in untreated and menadione treated BAECs.

OTHER EMBODIMENTS

It is to be understood that while embodiments have been described in conjunction with the detailed description thereof, the foregoing description is intended to illustrate and not limit the scope of the invention. Other aspects, advantages, and modifications are within the scope of the following claims.

What is claimed is:

1. A method for synthesizing an immunogen, comprising the steps of:
    selecting a peptide useful for immunization;
    adding the selected peptide to a buffer solution containing stoichiometric excesses of glutathione and aldrithiol, under constant stirring at room temperature, resulting in a glutathionylated peptide; wherein the selected peptide is actin;
    selecting a vaccine carrier protein;
    and conjugating the glutathionylated peptide to a vaccine carrier protein.

2. The method of claim 1, wherein: the actin peptide comprises residues 360 to 375 of SEQ ID NO: 2.

3. The method of claim 2, wherein:
    the actin peptide has a c-terminus thereof linked to 6-hydrazinonicotinamide (HyNic), forming a HyNic-GSS-actin peptide.

4. The method of claim 1, wherein:
    the buffer is Tris buffer (100 mM pH 7.5).

5. The method of claim 1, wherein:
    the vaccine carrier protein is keyhole limpet hemocyanin (KLH) that has been linked to 4-formybenzamide (4FB).

6. The method of claim 1, wherein:
    the selected peptide is an actin peptide comprising residues 360 to 375 of SEQ ID NO:2 and having a c-terminus thereof linked to 6-hydrazinonicotinamide (HyNic), forming a HyNic-GSS-actin peptide; and
    the selected vaccine carrier protein is keyhole limpet hemocyanin (KLH) that has been linked to 4-formybenzamide (4FB).

* * * * *